United States Patent [19]

Buckingham

[11] Patent Number: 4,556,560
[45] Date of Patent: Dec. 3, 1985

[54] METHODS FOR THE TREATMENT AND PROPHYLAXIS OF DIAPER RASH AND DIAPER DERMATITIS

[75] Inventor: Kent W. Buckingham, Cincinnati, Ohio

[73] Assignee: The Procter & Gamble Company, Cincinnati, Ohio

[21] Appl. No.: 460,692

[22] Filed: Jan. 24, 1983

[51] Int. Cl.$^4$ .................. A61K 33/24; A61K 33/30
[52] U.S. Cl. .................... 424/145; 424/131; 424/132; 424/147; 514/494; 514/502; 514/865; 15/206; 604/360
[58] Field of Search ............... 424/140, 141, 143, 145, 424/147, 312, 313; 604/360; 15/206 R

[56] References Cited

U.S. PATENT DOCUMENTS

| | | | |
|---|---|---|---|
| 2,856,330 | 10/1958 | Vagenius | 424/76 |
| 3,004,895 | 10/1961 | Schwartz | 604/360 |
| 3,964,486 | 6/1976 | Blaney | 128/284 |
| 3,996,346 | 12/1976 | Staffier et al. | 424/67 |
| 4,160,821 | 7/1979 | Sipos | 424/145 |
| 4,279,930 | 7/1981 | Hall et al. | 424/331 |
| 4,349,536 | 9/1982 | Hausler | 424/59 |
| 4,385,632 | 5/1983 | Odelhög | 604/360 |

FOREIGN PATENT DOCUMENTS 2080682 7/1981 United Kingdom .

OTHER PUBLICATIONS

Martindale, The Extra Pharmacopoeia, 26th Ed., pp. 270, 473–475, 585, (1975).
Lowenstein, Methods in Enzymology, vol. XIV, p. 176, (1969).
Goodman, et al., The Pharmacological Basis of Therapeutics, 5th Ed., pp. 946–947, (1975).
Jellnik, Formulation and Function in Cosmetics, p. 322, Wiley, (1970).
Banker, et al., Modern Pharmaceutics, p. 310, (1979).
The Merck Index, 9th Ed., p. 1232, (1976).
Physician's Desk Reference, 32nd Ed., p. 596, (1978).

*Primary Examiner*—Leonard Schenkman
*Attorney, Agent, or Firm*—George W. Allen; Jack D. Schaeffer; Steven J. Goldstein

[57] ABSTRACT

Methods for the treatment and prevention of diaper rash and diaper dermatitis caused by the prolonged contact of human skin with body waste are disclosed. The methods of the present invention employ the topical application of a minimum inhibitory concentration of a pharmaceutically-acceptable lipase-inhibiting agent to the area in need of such treatment, or the area where prevention is desired. The lipase-inhibiting agent is preferably a water-soluble metallic salt, such as $ZnCl_2$, and is preferably applied in combination with a barrier-like vehicle. The effectiveness of these methods is surprising in light of the present confusion and controversy surrounding the actual causes of diaper rash, and the heretofore unrecognized role of lipase as a factor in the cause of diaper rash and diaper dermatitis.

27 Claims, No Drawings

METHODS FOR THE TREATMENT AND PROPHYLAXIS OF DIAPER RASH AND DIAPER DERMATITIS

FIELD OF INVENTION

This invention relates to methods and compositions for the prevention and treatment of diaper rash.

BACKGROUND OF THE INVENTION

Diaper rash is a common form of irritation and inflammation of those parts of an infant's body normally covered by a diaper. It frequently occurs also in areas immediately adjacent to the diapered area. This condition is also referred to as diaper dermatitis, napkin dermatitis, napkin rash, and nappy rash.

The precise number of infants who suffer from diaper rash or diaper dermatitis is unknown. However, the United States Department of Health, Education and Welfare, has indicated that diaper dermatitis itself accounted for 97 visits to a doctor for every 1,000 infants in the United States between the ages of 0 to 2 years of age. See *Ambulatory Care Utilization Patterns of Children and Young Adults,* Vital and Health Statistics Series 13, Number 39, U.S. Department of Health, Education and Welfare, Public Health Service (1978). Further, while certainly more common in infants, this condition is not, in fact, limited to infants. Any individual who suffers from incontinence may develop this condition. This ranges from newborns, to the elderly, to critically ill or nonambulatory individuals.

It is generally accepted that true "diaper rash" or "diaper dermatitis" is a condition which is, in its most simple stages, a contact irritant dermatitis. See Jacobs, "Eruptions in the Diaper Area", *Pediatr Clin North Am* 25:209 (1978). The irritation of simple diaper rash results from extended contact of the skin with urine, or feces, or both. Diapers are worn to catch and hold the body waste, but generally holds the waste in direct contact with the skin until changed, i.e., in occluded fashion for long periods of time. The same is true for an incontinence pad, or incontinence brief. However, while it is known that body waste "causes" diaper rash, the precise component or components of the urine or feces which are responsible for the resulting irritation of the skin remain the subject of much controversy. The most commonly accepted list of factors linked to diaper rash includes ammonia, bacteria, the products of bacteria action, urine pH, *Candida albicans,* and moisture. These are generally cited in the art as being the most likely candidates. No conclusive investigations have been reported to date.

There are a host of conditions which are labeled (or more precisely mislabeled) "diaper rash" which may exhibit similar indications. In determining whether the condition that is being observed is actually diaper rash/dermatitis or some other condition no conclusive rule exists. If the dermatitis is limited to the diapered area and related to the use of the diaper or the contact of skin to body waste it can be safely concluded that the condition that exists is diaper dermatitis. There are a number of other conditions, however, which can begin in the area that is diapered on the infant, or which are simply more pronounced or aggravated in this area, but which are not truly "diaper rash" or "diaper dermatitis" in that they are not related to body waste contact. If the abnormal skin condition under scrutiny is present in locations other than in, or proximate to, the diapered area, e.g., the head, neck, extremities other than the genitalia, shoulders, etc., then one must consider other conditions, such as atopic dermatitis, seborrheic dermatitis, allergic contact dermatitis, psoriasis, scabies, bullous impetigo, papular urticaria, herpes simplex, and chemical or thermal burns. However, such observations are not conclusive because some diaper rash or diaper dermatitis conditions may have their genesis in the diapered area and then spread well beyond the diapered area.

This invention, and the accompanying discussion, deals only with compositions and methods for the treatment of diaper rash or diaper dermatitis, and other conditions which are associated with prolonged contact of the skin with urine, feces, or urine-feces mixtures, and/or the wearing of a diaper.

Weston, et al., "Diaper Dermatitis: Current Concepts", *Pediatrics* 66:4 (1980) has described and summarized the overall clinical features which can generally be associated with true diaper dermatitis. He has identified the forms of diaper rash or diaper dermatitis as follows:

Four clinical forms of diaper dermatitis felt to be related to diaper wear have been recognized. The most frequently observed is chafing dermatitis. This form demonstrates mild redness and scaliness seen over the buttocks, waist, and convex surface of the thighs where the diaper contacts the skin, or limited to the perianal area. Dermatitis limited to the perianal area is seen in the neonatal period, and the more widespread form is seen after 3 months of age. The second, and also frequently seen, form of dermatitis is a sharply demarcated confluent erythema with involvement of the skin folds with or without an accompanying whitish exudate. The third form of dermatitis is characterized by discrete shallow ulcerations scattered throughout the diaper area including the genitalia. In the fourth form, beefy red confluent erythema of the entire perineum with prominent elevated margins, satellite oval lesions around the periphery of the confluent area, and vesiculopustular lesions are described. This form is seen when the dermatitis becomes secondarily invaded with *Candida albicans.* Diffuse involvement of the genitalia in the inguinal folds is a regular feature of this form.

Thus, it is clear that diaper rash and diaper dermatitis may be merely a general inconvenience to the child, and, in turn, the parent. If left untreated, diaper rash and diaper dermatitis can result in masceration of the skin, thus leading to much more serious conditions and pathologies, e.g., infection, trauma, and systemic disease. See Burgoon, "Diaper Dermatitis", *Pediatric Clinics of North America* 18:835 (1961).

While no true causative agent has been identified, a diverse range of factors have been suspected of being associated with diaper rash and diaper dermatitis. Because these suspected agents all possess diverse properties and require such varied therapies, conventional methods of treatment for diaper dermatitis have been directed toward a straightforward attempt to minimize the contact of the skin with the feces or urine present in a soiled diaper. An artificial barrier is usually provided between the skin and the body waste to accomplish this. There have also been further attempts directed toward counteracting other suspected causes of diaper rash by promoting dryness in the diapered area, and preventing microbial growth and inflammation with conventional agents. Such a strategy would include frequent diaper changing, reduced use of plastic pants, triple diapering, careful washing and sterilization of diapers, treatment with an anti-Candidal agent, reduction of inflammation (by application of a topical application of a low potency glucocorticoid steroid), and the possible use of a bacteriostatic agent as a prophylactic measure in the diaper rinse. However, because the exact components of urine or feces which act as factors or cofactors contributing to diaper dermatitis have never been precisely identified, the most effective method of treating diaper dermatitis to date has been the artificial barrier. This had led to the frequent use of an occlusive, barrier-type topical, such as petrolatum or zinc oxide, to provide this protection, preventing the unknown offending component from coming in contact with the skin.

For example, Desitin ® ointment, (Leeming Division of Pfizer, Inc.) is probably the most common topical used in treating diaper rash. It contains both of the common barrier materials (zinc oxide and petrolatum) and additionally contains two common skin conditioning agents (cod liver oil and lanolin). All of these agents are commonly used in topical skin conditioning preparations.

Petrolatums, as well as zinc oxide, are well known to be highly effective barrier materials.

Zinc oxide is also known to be effective when applied externally—as a mild astringent for the skin, as a barrier material to prevent eczema, and also as a barrier protective to slight excoriations. It has been used in pastes and cremes in combination with many other topical actives. See Martindale, *The Extra Pharmacopoeia*, 26th Ed., p. 585, The Pharmaceutical Press (1975). Zinc oxide is almost totally insoluble in water.

Petrolatum (petroleum jelly; paraffin jelly; vasoliment; Vaseline) is commonly used as an occlusive barrier material in topical preparations. Petrolatum is a purified mixture of semi-solid hydrocarbons of the general formula $C_nH_{2n+2}$, when n is about 16 to about 32. Premium petrolatum is a white, semi-solid, unctious mass which is odorless and tasteless. It is a product of commerce.

Zinc glycerolate (the reaction product of zinc oxide and glycerine) is cited as being useful as a topical treatment for skin disorders, including ammoniacal dermatitis in babies in Patent Cooperation Treaty Application 8201-867. This disclosure indicates that the "zinc glycerolate" complex is insoluble in water. $CuCl_2$ is disclosed as a dye useful in this product. See, Patent Cooperation Treaty Application 8201-867, Taylor, filed Nov. 8, 1981, published June 10, 1982.

Zinc chloride is known as a powerful caustic and astringent. Its known uses include incorporation within mouthwashes, eye drops, and as deodorizer for foul smelling wounds and ulcers. See Martindale, *The Extra Pharmacopoeia*, 26th Ed., p. 270, The Pharmaceutical Press (1975).

U.S. Pat. No. 4,349,536, Hausler, issued Sept. 14, 1982, describes the use of zinc(II) and copper(II) trace minerals in a cream base to promote suntanning.

U.S. Pat. No. 4,160,820, Sipos, issued July 10, 1979, indicates that a glycerine solution containing about 0.5% to about 8% of a glycerine-soluble zinc salt is useful in the treatment of gingivitis when applied topically to the gums.

U.S. Pat. No. 3,996,346, Staffier, et al., issued Dec. 7, 1976, indicates that a combination of zinc oxide and zinc phenate $(Zn)(C_6H_5OH)_2$ is useful as a deodorant and an anti-perspirant when applied topically to the underarm area or the feet.

U.S. Pat. No. 3,964,486, Blaney, issued June 22, 1976, describes a disposable diaper or pad comprising an absorbent substrate having incorporated therein adipic acid in a quantity sufficient to inhibit ammonia formation and concomitant diaper rash. It describes the use of adipic acid in the diaper at a level sufficient to provide the urine with a pH in the range of about 3.5 to about 5.5 during use throughout the entire diaper upon wetting with urine.

A $CuSO_4/ZnSO_4$ combination is useful as a wet dressing in the treatment of eczema and impetigo in addition to being useful as a local astringent for eye infections. Martindale, *The Extra Pharmacopoeia*, 26th Ed., p. 475, The Pharmaceutical Press (1975).

Soluble metallic salts, particularly zinc, silver and lead ions, are known as lipase inhibitors. See Lowenstein, *Methods in Enzymology*, Vol. XIV, p. 176, Academic Press, (1969).

It is also known that the salts of copper are useful in topicals, astringents and fungicides. Martindale, *The Extra Pharmacopoeia*, 26th Ed., p. 473-475, The Pharmaceutical Press, (1975).

Polyethylene glycols (PEG's) are polymers produced by the reaction of ethylene oxide with ethylene glycol or water. PEG's with molecular weights up to about 600 are liquids at room temperature and they closely resemble highly-refined petrolatum/mineral oils in appearance and consistency. They are widely used as ointment bases for water-soluble agents. Goodman, et al., *The Pharmacological Basis of Therapeutics*, 5th Ed., p. 946-947, Macmillan Publishing Co. (1975).

Polyethylene glycol ointment, U.S.P., PEG 300, NF, PEG 400, U.S.P., PEG 600, U.S.P., are all listed in the cited official compendia. PEG's are known as agents with the ability to provide mechanical occlusive protection from dermal irritants. Jellinik, *Formulation and Function in Cosmetics*, p. 322, Wiley—Interscience, New York (1970).

The use of a 50:50, by weight, mixture of PEG 400:PEG 4000 as a topical vehicle for a water-soluble active is well-known. Banker, et al., *Modern Pharmaceutics*, Marcel Dekker, P. 310 (1979).

Triacetin, (1,2,3-propanetriol triacetate), is a colorless, oily liquid which is known as a topical anti-fungal. *The Merck Index*, 9th Ed., p. 1232, Merck and Co. (1976). The "self-regulating" action of triacetin is known, i.e., it is known that at the neutral (or higher) pH of the affected skin, glycerol and free fatty acid (acetic acid) are rapidly liberated from triacetin as a result of the action of the esterase enzymes found abundantly in skin, serum, and fungi. The growth of the fungi is inhibited by the free fatty acid. See, entry for Enzactin ® brand of triacetin, (Ayerst Laboratory Division of American Home Products), *Physician's Desk Reference*, 32nd Ed., p. 596 (1978).

Glycerol esters are known to be enzyme substrates, which, when acted upon by a hydrolyzing enzyme, will be hydrolyzed resulting in the release of free fatty acids.

SUMMARY OF THE INVENTION

Briefly, the present invention encompasses methods for the topical treatment and prophylaxis of diaper rash, diaper dermatitis, or other skin and skin tissue irritations associated with prolonged contact with urine or feces. This invention provides effective compositions and methods employing a pharmaceutically-acceptable lipase-inhibiting agent which reduces the action of lipase upon the skin in the affected area.

The compositions of this invention are useful in the treatment and prophylaxis of diaper rash or diaper dermatatis. They comprise a safe and effective amount of a pharmaceutically-acceptable lipase-inhibiting agent, such as a water-soluble metallic salt, incorporated at a level sufficient to deliver to the affected area a minimum inhibitory concentration of said lipase inhibitor, together with a barrier-like vehicle, which is capable of assisting the action of the lipase-inhibiting agent component by keeping it at the applied area in an active (i.e., able to inhibit lipase) form. A conventional vehicle such as a water-in-oil or oil-in-water emulsion utilizing petrolatum may also be employed. The compositions act to provide effective topical treatment and prophylaxis of diaper rash or diaper dermatitis by efficiently preventing the action of the irritation-causing component in urine and feces from acting upon the skin in the area subject to such irritation.

The methods of the present invention comprise the topical application of a pharmaceutically-acceptable lipase-inhibiting agent, such as water-soluble metallic salt, at its minimum inhibitory concentration (a level sufficient to inhibit the action of lipase from acting upon the skin in the area usually subject to such irritation).

The effectiveness of these methods are surprising in light of the present confusion and controversy surrounding the actual cause of skin irritation and diaper rash, and the heretofore unrecognized role of lipase in diaper rash and diaper dermatitis.

DESCRIPTION OF THE INVENTION

The methods of the present invention relate to methods of treating and preventing diaper rash and diaper dermatitis caused by the prolonged contact of human skin with body waste. The methods of the present invention require, at a minimum, the topical application of a minimum inhibitory concentration of a pharmaceutically-acceptable lipase-inhibiting agent to the area in need of treatment or the area where prevention is desired in a form such that it is available to inhibit the activity of the lipase present.

The compositions of the present invention are topical pharmaceutical compositions, which are useful in the treatment and prophylaxis of diaper rash and diaper dermatitis caused by prolonged contact of human skin with body waste, comprising about 0.1% to about 10% of a pharmaceutically-acceptable lipase-inhibiting agent selected from the group consisting of water-soluble metallic salts and about 90% to about 99.9% of a polyethylene glycol polymer.

The compositions of this invention require, at a minimum, (1) a safe and effective amount of a pharmaceutically-acceptable lipase-inhibiting agent which is effective in preventing the action of the enzyme lipase upon the skin when topically applied, and (2) a barrier-like pharmaceutical vehicle which is capable of delivering said agent to the applied area at at least said agent's minimum inhibitory concentration. The compositions of this invention may additionally employ other optional pharmaceutically-acceptable components which condition the skin, reduce skin irritation, which act as broad or narrow spectrum antimicrobials, which act as anti-inflammatory agents (such as low potency topical glucocorticoid steroids) to further promote healing, or which improve the cosmetic acceptability of the formulation. See also, abandoned U.S. patent application Ser. No. 460,696, filed Jan. 14, 1983, "Compositions and Methods for the Treatment and Prophylaxis of Diaper Rash and Diaper Dermatitis", Lawson, K. D., Buckingham, K. W., expressly incorporated herein by reference.

By the term "affected area", as used herein, is meant the area of human skin which is presently exhibiting any of the described levels of diaper rash or diaper dermatitis, or the area which will be in prolonged contact with urine or feces in an occluded fashion and at which a prophylactic effect is desired. It also includes the area immediately proximate to the described area. It is the area at which treatment, prevention, or both, is desired.

By the term "topical administration", or "topical application", as used herein, is meant directly laying on or spreading on epidermal tissue, especially outer skin.

By the term "safe and effective lipase-inhibiting agent", as used herein, is meant an agent which will provide sufficient inhibition or inactivation of the lipase enzymes to treat or prevent diaper rash or diaper dermatitis at a reasonable benefit/risk ratio attended with any therapeutic treatment. Within the scope of sound medical judgment, the lipase-inhibiting agent used will vary with the particular location of the condition being treated, the severity of the condition being treated, the expected duration of the treatment, any specific sensitivity to either the lipase-inhibiting agent itself, or the concentration of the lipase-inhibiting agent specific to the patient, the condition of the patient, concurrent therapies being administered, other pathologies or conditions present in the patient, and like factors within the specific knowledge and expertise of the patient or the attending physician.

By the term "pharmaceutically-acceptable", as used herein, is meant the ingredient modified by this expression is suitable for use in contact with the skin of humans at the cite where topically administered without undue toxicity, irritation, allergic response, and the like, commensurate with a reasonable benefit/risk ratio.

By the term "water-soluble", as used herein, is meant that the salt modified by this term is sufficiently soluble in an aqueous medium, at about 25° C. to about 40° C., such that it is capable of providing a concentration of the cation sufficient to substantially or completely inhibit the activity of the enzyme lipase.

By the term "lipase-inhibiting" or "lipase-inhibition", as used herein, is meant that the compound modified by this term demonstrates the ability to reduce the activity of lipase by at least about 50% or more as measured by a standard lipase activity methodology. For example, the method of commerce available from Harleco ® diagnostics utilizes the activity of lipase, i.e., the digestion of triglycerides to diglycerides and monoglycerides, glycerol and free fatty acids. After this digestion is allowed to proceed at the optimal buffered pH, the turbidity is measured spectrophotometrically at 400 nanometers.

By the term "minimum inhibitory concentration", as used herein, is meant sufficient lipase-inhibiting agent to reduce the activity of the lipase present by at least 50% as measured by standard lipase activity measurements, such as the Havoco ® diagnostic procedure described above.

By the term "safe and effective amount of a pharmaceutically-acceptable lipase-inhibiting agent", as used herein, and as applied to the compositions of the present invention, is meant that a sufficient amount of lipase-inhibiting agent is incorporated within the composition such that when topically applied, the composition is able to deliver to the applied site at least the minimum inhibitory concentration of the selected lipase-inhibitor agent.

By the term "effective amount of a skin cleansing agent", as used herein, is meant an amount of cleansing agent which will aid in removing body waste and other irritants without itself causing undue irritation or dryness.

LIPASE-INHIBITING COMPOUNDS

Lipase (triacylglycerol lipase) is the trivial or common term employed to represent what is in fact a group of enzymes belonging to the esterases. Their general activity is to hydrolyze fats present in the ester form (such as the glycerides found in human skin), and accordingly generate fatty acids and glycerol. Because this group of enzymes is so widely distributed in plants, molds, bacteria, milk, and milk-products, as well as in almost all animal tissues, they are almost always present in the diapered area when it has been soiled by human waste. Most of the enzymes have a broad pH optimum between 7.5 and 9.5. See, Mattson, et al., "Carboxylic Ester Hydrolases in Rat Pancreatic Juice, *J. Lipid R.*, 7:536 (1966).

While not intending to be bound or limited by theory, it is thought that the surprising utility of the lipase-inhibiting agent or lipase inhibitors, particularly the soluble salts of lipase-inhibiting metallic ions, in the treatment and prophylaxis of diaper rash is attributed to the heretofore unrecognized high degree of irritation directly resulting from action of lipase upon the skin are exposed to a soiled diaper.

It is well-known that one of the most important functions of the skin is to act as a barrier to the egress of physiologic fluids, electrolytes and other components, as well as to act as a barrier to the ingress of microbes, toxins, and other inflammatory or harmful agents. In light of the present discovery that the activity of lipase contributes to almost all diaper rash, it is thought that in addition to causing irritation by the digestive degenerative action of lipase on the skin per se, the action of breaking down the skin components compromises the barrier property of the skin in the affected area. This breakdown of the integrity of the skin allows other components of urine and feces, which may not, by themselves, be irritating, to migrate through the compromised skin. At this point normally harmless components may then become irritating. When employing the compositions and methods of the present invention, the lipase is inactivated. It is thereby prevented from acting upon the skin and causing irritation. Such inactivation of lipase prevents the compromise of the barrier function of the skin which in turn prevents irritants (such as fungi, bacteria, and bile salts and acids) from migrating through and further irritating and inflamming the skin.

The mere application of a barrier material, such as petrolatum, may, for a limited time, provide the same result. Such a barrier would physically prevent the lipase present in the body waste from coming in contact with the skin. However, this can only be accomplished for a very short duration. The amount of barrier material (without a lipase inhibitor) which would have to be applied to achieve the efficacy of the present invention would effectively prevent the dynamic interaction between the skin and the environment, leading to skin irritations and pathologies perhaps more serious than diaper rash or dermatitis. No reasonable amount of barrier material alone could be applied which would provide the complete, uniform and prolonged level of protection as is afforded by the compositions and methods of the present invention.

Once the lipase has been allowed to come in contact with the skin and has begun to digest components of the skin—and accordingly compromised its barrier properties—further application of barrier may merely serve to trap irritants and force their migration through the skin.

The lipase-inhibiting agents or lipase-inhibitor compounds useful in the methods and compositions of the present invention can be described as agents which are capable of substantially or completely inhibiting the activity of the enzyme lipase, preventing it from acting upon the esters of the skin, when topically applied at pharmaceutically- and dermatologically-acceptable levels at any pH, but particularly at a pH of about 7.5 to about 9.5.

Agents which are known to inhibit the action of lipase, and which are useful as lipase-inhibiting agents in the compositions and methods of the present invention, include, without limitation, the water-soluble (as defined herein) salts of metals including cadmium, cobalt, copper, lead, mercury, molybdenum, nickel, silver, lanthanum, tin and zinc. Mixtures may also be employed. Agents which are known to inhibit the activity of lipase, and which are preferred in the compositions and methods of the present invention, include zinc chloride, zinc acetate, zinc nitrate trihydrate, zinc nitrate hexahydrate, zinc sulfate, zinc sulfate heptahydrate, zinc sulfate hexahydrate, iron(II)chloride, iron(II)chloride tetrahydrate, iron(III)chloride, iron(III)chloride monohydrate, iron(III)chloride hexahydrate, iron(II)lactate, iron(III)lactate, iron(III)malate, iron(II)nitrate, iron(III)nitrate hexahydrate, iron(III)nitrate.9H$_2$O, iron(II)sulfate and its hydrates, iron(III)sulfate and its hydrates, copper sulfate pentahydrate, tin chloride, cobalt chloride and lanthanum chloride. Zinc salts of both the saturated and unsaturated monocarboxylic acids having about 6 to about 12 carbon atoms are also preferred. Those having about 8 to about 10 carbon atoms are highly preferred. Mixtures of the above may also be employed.

The insoluble salts of the metals first recited above fail to be useful in the present invention. For example, zinc carbonate and zinc oxide are ineffective in the inhibition of lipase because of their inability to provide the critical level of free metal ion, $Zn^{++}$. The ability to generate, the free metal ion in an aqueous environment at about 25° C. to about 45° C. in sufficient concentration to substantially inhibit lipase activity at a pH of about 7.5 to about 9.5, or lower, is critical, and accordingly, critical to being useful in the present invention.

Lipase inhibiting agents particularly preferred in the practice of the present invention include zinc chloride, zinc sulfate, iron(II)chloride, iron(III)chloride, tin chloride, copper sulfate, the zinc salts of monocarboxylic fatty acids having from about 6 to about 10 carbon atoms, hydrates thereof, and mixtures thereof. Of the above, zinc chloride is the most highly preferred.

The lipase-inhibiting agents useful in the present invention are those which, when topically applied neat, or when topically applied suspended, dispersed or dissolved in a pharmaceutically-acceptable topical vehicle, can provide the minimum inhibitory concentration to the affected area. The selection of such a lipase-inhibiting active will, of course, depend on many factors. These would include the nature and composition of the vehicle selected, the amount or absence of water in the selected vehicle, the safety and efficacy record of the particular active selected, and, of course, the availability and expense of the actives.

Lipase inhibitors useful in the present invention include those which act as a substitute substrate. That is, compounds which are, themselves, triacyglycerol esters and which the lipase will act upon and digest rather than those which are present in the skin and which contribute to its barrier properties. Accordingly, preferred as lipase-inhibiting agents useful in the compositions and methods of the present invention include the glyceryl esters of the general formula:

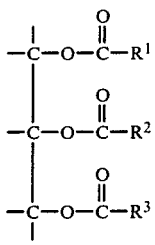

wherein $R^1$, $R^2$ or $R^3$ are independently alkyl, or alkenyl, branched- or straight-chain groups having from about 1 to about 18 carbon atoms. Lipase inhibiting agents of this formula above which have about 4 to about 10 carbon atoms are preferred, and those having about 6 to about 10 carbon atoms are highly preferred.

The lipase-inhibiting agents of the compositions and methods of the present invention are used at levels which are safe and which provide substantial or complete inhibition of lipase when topically applied to the affected area. It will be appreciated by the skilled artisan that this level will depend upon the overall efficacy of the lipase inhibitor selected. When dealing with the water-soluble metal salts in the methods of the present invention, for example, the level applied is generally in the range of an amount which results in a concentration of free metal ion equivalent to about 10 millimoles of ion per liter of available water to about 1,000 millimoles (1 mole) of metal ion per liter of available water at the effected area, or a level which is equivalent to an aqueous solution of about 10 millimolar to about 1,000 millimolar (millimoles of metal ion per liter of solution) in the affected area. When using a conventional pharmaceutical topical vehicle to formulate compositions useful in the methods of the present invention, this will generally be in the range of about 0.1% to about 10% by weight of lipase-inhibiting agent. Preferred lipase inhibitor levels are about 1% to about 5% of the overall composition. Levels of about 2% to about 4% by weight of the overall composition are highly preferred. However, it will be appreciated that the upper level will be limited only by safety and economy.

The lipase-inhibiting agents of this invention are typically applied from one to twelve times daily, usually at the time the diaper or incontinence pad is changed or checked. It is applied to the affected area, that is, the area in need of the treatment or prevention. When prevention is desired, the lipase-inhibiting agents are applied to any area which is or may be exposed to body waste, as well as the area proximate to this exposed area.

The skilled artisan will appreciate that this application rate will vary with the severity of the condition being treated, its progress, the total surface area that it has involved, the frequency and duration of past dermatitis and rash incidence, and the average length of exposure of the skin to body waste. It is, however, critical that the rate of application be such that a minimum inhibitory concentration of lipase inhibitor be applied to the affected area. For example, the last application of the day may be at a rate significantly greater than those during the day due to increase in the amount of time that the area may be exposed during sleep. At such times, usage rates of up to concentrations of about 5M may be employed. Preferred usage rates for the lipase-inhibiting agents of the present invention are rates of about 50 mM to about 1000 mM concentrations to the affected area. Further, the minimum inhibitory concentration of some lipase-inhibiting agents may be greater than for others. The potency of the lipase-inhibiting agent selected must also be taken into consideration. For example, when $ZnCl_2$ is selected as the lipase-inhibiting agent, it is preferred that the delivery concentration is about 10 mM or greater, and more preferably about 50 mM or greater, of $ZnCl_2$. However, when $FeCl_3$ is selected as the lipase-inhibiting agent, it is preferred that the delivery concentration be about 50 mM or greater, and more preferably about 100 mM or greater, of $FeCl_3$. Levels of greater than about 1,000 mM (1M) generally serve only to increase possible irritation.

The concentration, of course, should be optimized. Once the lipase inhibitor is selected for application, the skilled artisan can determine the concentration which will completely inhibit the activity of lipase at the affected area for the desired period of time, while at the same time provided a minimized risk of irritation or adverse reaction.

The lipase-inhibiting agent can be applied at intervals ranging from about once every twenty-four hours to about once every hour. Application intervals of about every 2 hours to about every six hours are preferred. Such an application interval maximizes the therapeutic effects of the lipase-inhibiting agent while minimizing the inconvenience. A second preferred application interval is to apply the lipase-inhibiting agent every time the diaper is changed, or every other time the diaper is changed. It may also be applied at a time that the diaper is checked for waste. This is also appropriate for applications to adult individuals who are using an incontinence pad or brief.

However, any treatment or application regimen which provides the minimum inhibitory concentration of a pharmaceutically-acceptable lipase-inhibiting agent can be employed using the methods of the present invention.

VEHICLE

In the methods of the present invention, any pharmaceutically-acceptable vehicle may be employed to assist in the delivery of the lipase-inhibiting agent. Such vehicles include ointments, creams, pastes, or other semi-solid vehicles. While purely solid (e.g., powders) or purely liquid (fluid) systems may be used, these are generally not as desirable as semi-solid vehicle formulations because of the overall inability of such vehicles to cling to the surface of application for a protracted period as well as their inability to deliver safe and effective levels of the lipase-inhibiting agents of the present invention. Semi-solid preparations have better staying properties and are better able to consistently deliver the required safe and effective lipase-inhibiting agent levels. It is desirable to keep the lipase inhibitor available for the longest possible period of time at the affected area. It is for this reason also that the semi-solid preparations are preferred. However, any vehicle or preparation which is capable of delivering the minimum inhibitory concentration of the selected lipase inhibitor to the affected area, or to the diapered area, can be used.

Ointments useful in the practice of the methods of the present invention include, generally, hydrocarbon-based semi-solids in which the lipase inhibitor can be dissolved or dispersed. They are viscous in nature. Generally, $C_{16}$ to $C_{30}$ straight and branched chain hydrocarbons are entrapped in a fine crystalline matrix of $C_{30}$ to $C_{50}$ hydrocarbons. The latter, having high melting and solidifying points, and being solids at room temperature, give the ointment a good deal of staying ability. White and yellow petrolatum are examples of such systems. In addition, such vehicles provide excellent barrier properties, preventing the lipase present in a soiled diaper from contacting the skin, and giving the lipase-inhibiting agent the maximum amount of time to fully inhibit the lipase's activity.

Such ointments can be made by incorporating high melting waxes into fluid mineral oil by fusion followed by cooling. They may also be made by incorporating polyethylene into mineral oil at high temperatures followed by rapid cooling. The lipase-inhibiting agent is dispersed within the composition.

Silicon ointments are also useful. Such ointments contain polydimethylsiloxane oil in place of all or part of the lower molecular weight hydrocarbon component in the vehicles described above.

Preferred ointments useful in the present invention include polyethylene glycol ointments. Such preparations are generally considered to be water-soluble systems which contain fluid, short chain polyethylene glycol polymers of low molecular weight which are liquid at room temperature, within a crystalline network of high melting point, long chain polyethylene glycol polymer which are solid at room temperature. While the nature of the structure is very much analogous to that of petrolatum, such a system possesses significantly different solubility properties. It is well-known that many drugs which are relatively insoluble in petrolatum are readily dissolved in such a vehicle base. An added advantage is that because polyethylene glycols are very soluble in water, the base is easily washed off the skin. Such a vehicle is useful in attempting to deliver the water-soluble metal salt lipase-inhibiting agent of the present invention. In addition, because it is closely analogous to petrolatum, such a vehicle base possesses excellent barrier properties.

A second preferred ointment base for the methods of the present invention include absorption bases. Absorption bases are ointments which contain additional ingredients which result in properties very similar to the hydrocarbon and silicone ointments described above, which additionally possess the ability but to emulsify a significant quantity of water. Water-in-oil (W/O) emulsions are thus formed. The oil-type external phase results in a composition which retains strictly ointment-like characteristics. Water-soluble lipase-inhibiting metallic salts can be incorporated into these vehicles. They may be fully dissolved within the emulsified aqueous phase and/or dispersed within the continuous lipid phase. In general, the aqueous internal phase is used to dissolve the water-soluble metallic salts when such compounds are selected as the lipase-inhibiting agent in the practice of the present invention.

The advantage of both the polyethylene glycol ointment, and the emulsion type absorption bases, when used in the practice of the methods and compositions of the present invention, is that both are capable of providing a significant amount of high molecular weight hydrocarbon to provide an effective barrier when applied, while at the same time retaining the ability to incorporate and deliver the water-soluble lipase inhibitors.

Pastes may also be employed in the practice of the present invention. Pastes are ointments which contain a high percentage (up to about 50%) of insoluble solids. Their rheological properties are significantly different than ointments due to this high percentage of solids. They are much stiffer, and often have a particulate matrix which aids in their adherence. The solids used often include starch, zinc oxide, calcium carbonate and talc. Pastes possess exceptional protective barrier properties, and also possess the ability to absorb noxious or undesirable components which are generated in situ. Accordingly, pastes are also preferred in the present invention. The lipase-inhibiting agent is dissolved within the paste if possible. Any or all of the lipase-inhibiting agent not soluble in the paste may be suspended like the other solids.

Creams are also useful in the practice of the present invention. Like water-in-oil ointments, oil-in-water creams provide both a high melting point waxy component for improved barrier properties as well as an aqueous component for aiding in the incorporation of, and delivery of, the lipase inhibitor. Also, like ointments, they possess both a hydrophilic and lipophilic phase so that either or both types of lipase inhibitor can be employed. Typically, the larger the percentage of the internal phase, the more effective the barrier property of the cream as it is the internal phase of a cream which is the high molecular weight component. Creams which have an internal percentage of oil (such as waxy alcohols or waxy acids) of from about 20% to about 40% by weight are preferred when a cream is employed.

Gels and rigid foams may also be used as vehicles to incorporate the lipase-inhibiting agents of the present invention.

Formulation of such vehicles can be performed in accordance with conventional methods such as those found in Banker, et al., *Modern Pharmaceutics*, Marcel Dekker, Inc., pgs. 263–327, (1979), expressly incorporated herein by reference.

The compositions of the present invention are preferably of the polyethylene glycol ointment variety. Such compositions are the most desirable because of their ability to provide a "zone of inhibition" between body waste and the skin through which the lipase must pass to reach the skin. In addition to possessing a high degree of cosmetic acceptability, such compositions possess the ability to "stay" on the skin, and to provide the lipase-inhibiting agents in an effective form, over a prolonged period of time, within this "zone of inhibition". No other composition has been found to date which possesses these unique properties. These compositions comprise about 0.1% to about 10% of a lipase-inhibiting agent selected from the group consisting of water-soluble metallic salts, and about 90% to about 99.9% of a polyethylene glycol polymer. The polyethylene glycol polymer portion of this composition is preferably a mixture of short chain, polyethylene glycol polymers which are liquid at room temperature and high melting long chain polyethylene glycol polymers. The lower molecular weight polyethylene glycols ae selected from those which have an average molecular weight of about 200 to about 600; the high molecular weight polyethylene glycol polymers are those selected which have an average molecular weight of about 2,000 or greater, preferably about 3,000 or greater, and, more preferably, the high molecular weight polyethylene glycol has an average molecular weight of about 4,000 to about 6,000. These are present at a ratio of short chain polyethylene glycol polymers: long chain polyethylene glycol polymer of about 80:20 to about 50:50, preferably about 70:30 to about 50:50 and most preferably about 70:30 to about 60:40, by weight, of the vehicle.

The lipase-inhibiting agents useful in the compositions of the present invention are selected from the group consisting of water-soluble metallic salts of cadmium, cobalt, copper, lead, mercury, molybdenum, nickel, silver, lanthanum, tin and zinc, as well as mixtures thereof. Preferred lipase-inhibiting agents useful in the compositions of the present invention include zinc chloride, zinc acetate, zinc nitrate trihydrate, zinc nitrate hexahydrate, zinc sulfate, zinc sulfate heptahydrate, zinc sulfate hexahydrate, iron(II)chloride, iron(II)chloride tetrahydrate, iron(III)chloride, iron(III)chloride monohydrate, iron(III)chloride hexahydrate, iron(II)lactate, iron(III)lactate, iron(III)malate, iron(II)nitrate, iron(III)nitrate hexahydrate, iron(III)nitrate.$9H_2O$, iron(II)sulfate and its hydrates, iron(III)sulfate and its hydrates, copper sulfate pentahydrate, tin chloride, cobalt chloride and lanthanum chloride. Zinc salts of the monocarboxylic acids having about 6 to about 12 carbon atoms are also preferred. Those particularly useful in the composition of the present invention include zinc chloride, zinc sulfate, iron(II)chloride, iron(III)chloride, tin chloride, copper sulfate, the zinc salts of monocarboxylic fatty acids having from about 6 to about 10 carbon atoms, hydrates thereof, and mixtures thereof.

It will be appreciated that the compositions of this invention also provide a method for treating and preventing diaper rash and diaper dermatitis caused by prolonged contact of human skin with body waste comprising topically applying to an area in need of such treatment or prevention an amount of the composition sufficient to supply a minimum inhibitory concentration of the metallic salt lipase-inhibiting agent.

The compositions of this invention are typically applied about one to about 12 times daily, usually at the time the diaper or incontinence pad is changed or checked. It is applied to the affected area. When prevention is desired, the compositions are applied to any area which is or may be exposed to body waste, as well as the area proximate to this exposed area.

Typical safe and effective usage rates are about 3 mg to about 10 mg of total composition per square centimeter of skin. While the skilled artisan will appreciate that this application rate will vary with the severity of the condition being treated, its progress, the total surface area that it has involved, the frequency and duration of past dermatitis and rash incidence, the potency of the lipase inhibitor selected and the average length of exposure of the skin to body waste, it is, however, critical that the rate of application be such that a minimum inhibitory concentration of lipase inhibitor be available for delivery to the affected area. For example, the last application of the day may be at a rate significantly greater than those during the day due to increase in the amount of time that the area may be exposed during sleep. At such times, usage rates of up to about 250 mg of total composition per square centimeter of skin may be applied when the degree of occlusion desired is high.

The compositions can be applied once every twenty-four hours to about once an hour. Application intervals of every 2 hours to about every six hours are preferred. Such an application interval maximizes the therapeutic effects of the compositions while minimizing the inconvenience. A second preferred application interval is to apply the composition at every or every other diaper change, or at the time the diaper is checked for waste. This is also appropriate for applications of adult individuals who are using an incontinence pad or brief.

However, any treatment or application regimen which provides sufficient composition to deliver a minimum inhibitory concentration of a pharmaceutically-acceptable water-soluble metallic salt lipase-inhibiting agent can be employed using the compositions of the present invention.

Other optional components well-known in the art can be added to the formulations or the compositions of the present invention to enhance their efficacy and cosmetic acceptability. Glucocorticoid steroids, anti-fungal agents, and skin conditioning agents may be added to the compositions of the present invention. Further optional components can be added to the formulations of the present invention to enhance their cosmetic acceptability. Such components include thickening agents, pigments, opacifiers, fragrances, perfumes, and the like. Such materials, when added, should not unduly interfere with the ability of the composition to provide the minimum inhibitory concentration of the lipase-inhibiting agent. Such formula modifications to improve cosmetic acceptability are well within the skill of the workers in the cosmetic and dermatological arts and, by themselves, do not constitute a part of the present invention.

All optional components should be selected to prevent substantial interference with the ability of the composition to deliver a minimum inhibitory concentration of the selected lipase-inhibiting agent.

The lipase-inhibiting agents of the present invention can also be incorporated into, or delivered from, diapers, particularly disposable diapers, incontinence pads, or wipes.

The particular diaper structure is not critical to the practice of the present invention. The only essential structural element is an absorbent substrate in a pad or disposable sheet configuration. Representative examples of suitable diaper structures are fully described in U.S. Pat. No. Re 26,151, Duncan, et al., issued Jan. 31, 1967; U.S. Pat. No. 3,592,194, Duncan, issued July 13, 1971; U.S. Pat. No. 3,489,148, Duncan, et al., issued Jan. 13, 1970; and U.S. Pat. No. 3,964,486, Blaney, issued Jan. 22, 1976; which are incorporated herein by reference. A preferred disposable diaper for the purpose of this invention comprises an absorbent core; a topsheet superposed or co-extensive with one face of said core; a liquid impervious backsheet superposed or co-extensive with the face of said core opposite the face covered by said topsheet; said backsheet most preferably having a width greater than that of said core thereby providing side marginal portions of said backsheet which extend beyond said core, said margin portions being folded around and on top of the edges of said absorbent core.

The diaper is preferably folded in a box pleat configuration.

The absorbent core substrate can be constructed from highly absorbent essentially hydrophilic fiber aggregates which act as a reservoir for excreted waste fluid. For example, this layer can consist of piles of creped cellulose wadding. Fibers which are useful herein can be classified according to origin as wood, rag, cotton linters, straw or espardo and according to manufacturer as mechanical, chemical, semi-chemical, unbleached, semi-bleached, or bleached. Preferred absorbent structures are prepared from wood, cotton or cotton linters.

The lipase-inhibiting agents of the present invention are incorporated into the diaper structure, preferably into the absorbent core substrate or topsheet. The lipase-inhibiting agent may be incorporated into the diaper structure by diverse methods which will be readily apparent to those skilled in the art. For example, the lipase-inhibiting agent can be dispersed in a pharmaceutically- or dermatologically-acceptable aqueous or volatile carrier such as water, ethanol, or the like, and applied to the diaper topsheet, to the absorbent core, or to the core side of the backsheet, by spraying, dipping, printing, soaking or otherwise contacting the selected structural element of the diaper with the lipase-inhibiting agent and its carrier.

Normally, the lipase-inhibiting agent is incorporated into the diaper structure in an amount which will deliver the minimum inhibitory concentration of the selected agent to the skin when wetted with urine. As will be appreciated by those skilled in the art, diapers designated "daytime diapers" in the art preferably incorporate lower levels of the lipase-inhibiting agent than diapers which by virtue of their greater bulk and absorptive capacity are designated "nighttime diapers" or "toddlers' diapers" and are intended for overnight use.

The particular wipe structure is also not critical to the practice of the present invention. The only essential structural element is in absorbent material into which a lipase-inhibiting agent may be releasably incorporated. A preferred wipe for the purpose of this invention comprises an absorbent fibrous material or core into which the lipase-inhibiting agent may be releasably incorporated. A highly preferred disposable wipe for the purposes of this invention comprises an absorbent fibrous material and a feces-impermeable backing material; said backing being superposed or co-extensive with one face of said absorbent fibrous material; said backing material most preferably being a web-backing material and most preferably having a width greater than said absorbent material providing side marginal portions which extend beyond said absorbent material, said margin portions being folded around and on top of the edges of said absorbent material. The selected lipase-inhibiting agent may be releasably incorporated into the wipe structure by diverse methods which will be readily apparent to those skilled in the art. For example, the lipase-inhibiting agent can be dispersed in a dermatologically-acceptable aqueous or volatile carrier such as water, ethanol, or the like, and applied to the absorbent material by spraying, dipping, printing, soaking or otherwise contacting the absorbent material of the wipe with the lipase-inhibiting agent and its carrier. A skin cleansing agent, preferably an oleaginous cleansing agent, may optionally be releasably incorporated into the absorbent material as well.

The wipes described above provide a method for treating and preventing diaper rash, or diaper dermatitis, caused by prolonged contact of human skin with body waste comprising contacting the area in need of such treatment or prevention with the wipe.

HAIRLESS MOUSE PATCH TEST

This method may be used to determine the utility and effect of lipase-inhibiting agents, or compositions containing these agents, on primary skin irritation caused by prolonged contact of a urine/feces mixture under occluded conditions.

Male, hairless mice at 8–12 weeks of age are used for the study. The animals are housed individually in plastic shoe box cages for the experiments, and fed Purina ® Rodent Laboratory Chow and tap water ad libitum. Mice are assigned numbers during each study which are posted on each cage.

The mice are cared for, and the room conditions maintained following acceptable animal study conditions.

Patch treatment compositions are prepared by taking the fecal material to be tested and mixing it with a 2% urea solution at a weight:weight ratio of 1:4 feces:urea. 0.1 ml of the lipase-inhibiting agent solution or composition of the desired concentration is patched along with 0.375 ml of the urine/feces mixture. Patches for the mice are prepared by saturating an absorbent material (such as cotton) with the feces/urine suspension, placing it on the skin and covering it with an impermeable material. For example, this may be done by cutting away the adhesive border from a 37×20 mm Webril pad. The Webril pad will then be cut into quarters to obtain 1 $cm^2$ patches. Each patch will be saturated with 0.1 ml of the lipase-inhibiting agent solution and 0.375 ml of the urine/feces mixture. The control patch is simply 0.375 ml of the urine/feces mixture. Prior to application of test or control patches, each mouse is anesthetized by placement into a chamber containing ether. The test patch is then placed midline on the mouse back, towards the shoulder, and covered with Blenderm ® (3M) tape in order to occlude the patch site. The mouse is next wrapped with Scanpor ® tape (Norgeplaster A/S) to secure the patch. After 24 hrs., the initial patch is removed and a fresh patch of test substance or a fresh control is applied, as described above. After 24 hrs., the second patch is removed, thus giving a total occluded patch time of 48 hrs.

Approximately 1 hr. after removal of the second patch, the test site skin condition is evaluated using the grading scales outlined in the following tables:

| (1) Erythema Formation | |
|---|---|
| No erythema | 0 |
| Very slight erythema | 1 |
| Well defined erythema | 2 |
| Moderate to severe erythema | 3 |
| Severe erythema (beet redness) | 4 |
| (2) Eschar Formation | |
| No eschar | 0 |
| Slight eschar | 1 |
| Moderate eschar | 2 |
| Severe eschar | 3 |
| (3) Edema Formation | |
| No edema | 0 |
| Very slight edema (barely perceptible) | 1 |
| Slight edema (edges of area well defined by definite raising) | 2 |
| Moderate edema (raised approximately 1 mm) | 3 |
| Severe edema (raised more than 1 mm and extending beyond area of exposure) | 4 |

Each animal is examined by two graders, at least one of whom is blind as to the treatments applied. Both graders' scores should be calculated for each of the above categories, as well as a primary Irritation Index equalling the sum of scores for each category.

GUINEA PIG PATCH TEST

This method may be used to determine the effect and utility of lipase-inhibiting agents or compositions containing said agents, on the level of primary irritation of guinea pig skin induced by occlused conditions, indicating utility in the present invention.

Hartley guinea pigs, approximately 350 to 450 grams, males and females are used for the study.

Patch treatment compositions are prepared by taking fecal material and mixing it with a 2% urea solution at a weight:weight ratio of 1:4 feces:urea. 0.1 ml of the lipase-inhibiting agent solution or composition is patched along with 0.375 ml of the urine/feces mixture. The control patch is simply 0.375 ml of the urine-feces mixture.

Test patches are applied to the upper right or left dorsal quadrant of the guinea pig. Two patches are applied to each animal. Five or more patch sites are used to evaluate each preparation.

Twenty-four hours prior to patching the test animals, they are clipped and depilated using a commercial depilatory. Upon removal of the depilatory, the sites are thoroughly washed with warm water. The animals are allowed to rest overnight.

On the day of the test, 0.1 ml of the test composition is applied to an area about 1–1.5 in. in diameter on either side of the spine. The test sites may be covered with a non-absorptive, non-woven fabric taped around the sites for a prescribed time prior to patching with the irritant, or, if appriopriate, immediately patched with 0.375 ml of feces/urea suspension. This patching can be carried out by using a Hill Top ® chamber, a molded plastic chamber which conforms to the contours of the skin. The chamber contains a cotton pad which is saturated with the feces/urea mixture. The pad is sandwiched between squares of release paper and occlusive hypoallergenic adhesive tape. The patches are held in position by wrapping the animal with Micropore ® surgical tape. After 24 hours, the patches are removed and residual fecal matter carefully removed with water and paper towels. After approximately 24 additional hours, during which time transient irritation may dissipate, the test sites are graded for irritation using the following scale for guidance in assigning a numerical grade to the primary irritation present. Each site is evaluated for the presence of erythema, eschar, and edema by 2 graders. The site grade, or primary Irritation Index, is calculated for each site by summing the scores for each of these three conditions. A mean of the Irritation Index of 5 sites is used in determining the relative effectiveness of any treatment.

Approximately 24 hours after the patches have been removed, evaluate the test sites, with the option of using half grades, and report the results on the basis of the table given below. This evaluation will be reported as the 24-hour post-treatment evaluation.

| (1) Erythema Formation | |
| --- | --- |
| No erythema | 0 |
| Very slight erythema | 1 |
| Well defined erythema | 2 |
| Moderate to severe erythema | 3 |
| Severe erythema (beet redness) | 4 |
| Highest possible erythema score | 4 |
| (2) Eschar Formation | |
| No eschar | 0 |
| Slight eschar | 1 |
| Moderate eschar | 2 |
| Severe eschar | 3 |
| Highest possible eschar score | 3 |
| (3) Edema Formation | |
| No edema | 0 |
| Very slight edema (barely perceptible) | 1 |
| Slight edema (edges of area well defined by definite raising) | 2 |
| Moderate edema (raised approximately 1 mm) | 3 |
| Severe edema (raised more than 1 mm and extending beyond area of exposure) | 4 |
| Highest possible edema score | 4 |

The following non-limiting Examples (I–IX) demonstrate the efficacy of the methods of the present invention. In Examples I–V, fecal material is mixed with a 2% urea solution at a weight:weight ratio of 1:4 feces:urea, and this homogenate is patched as described above in the Hairless Mouse model with 0.375 ml of this homogenate. The pure homogenate is patched as the control. Where a specific concentration of lipase-inhibiting agent is expressed, the feces/urea homogenate is patched in combination with 0.1 ml of a solution of the described lipase-inhibiting agent solution.

In Examples VI and VII, a stool-free and urine-free pure lipase composition of the expressed activity is patched in the Hairless Mouse model as described above. This is the Control. This lipase composition is patched in combination with 0.1 ml of the lipase-inhibiting agent solution at the concentration expressed.

EXAMPLE I

| PATCH | RELATIVE LIPASE ACTIVITY | IRRITATION INDEX |
| --- | --- | --- |
| Control | 6250 | 7.20 ± 0.75 |
| 10 mM $ZnCl_2$ | 5000 | 6.05 ± 1.23 |
| 25 mM $ZnCl_2$ | 0 | 4.95 ± 1.36 |
| 50 mM $ZnCl_2$ | 0 | 0.80 ± 1.01 |
| 100 mM $ZnCl_2$ | 0 | 1.15 ± 0.97 |
| 10 mM $CuSO_4.5H_2O$ | 4750 | 6.75 ± 1.42 |
| 25 mM $CuSO_4.5H_2O$ | 2250 | 5.35 ± 2.93 |
| 50 mM $CuSO_4.5H_2O$ | 750 | 3.50 ± 3.08 |
| 100 mM $CuSO_4.5H_2O$ | 0 | 5.50 ± 1.05 |

The above example demonstrates the surprising ability of lipase-inhibiting agents to significantly reduce the irritation caused by prolonged, occluded contact by urine and feces to the skin when applied at the minimum inhibitory concentration, or above, in the methods of the present invention. The above example also demonstrates the role of lipase in causing such irritation. Further, the above example demonstrates the variance in potency for various lipase-inhibiting agents.

EXAMPLE II

| PATCH | RELATIVE LIPASE ACTIVITY | IRRITATION INDEX |
| --- | --- | --- |
| Control | 6000 | 6.67 ± 0.94 |
| 20 mM $ZnCl_2$ | 500 | 3.50 ± 2.44 |
| 30 mM $ZnCl_2$ | 1250 | 4.87 ± 1.37 |
| 40 mM $ZnCl_2$ | 0 | 2.62 ± 1.86 |

| PATCH | RELATIVE LIPASE ACTIVITY | IRRITATION INDEX |
|---|---|---|
| 50 mM $ZnCl_2$ | 0 | 2.54 ± 1.78 |
| 60 mM $ZnCl_2$ | 0 | 1.42 ± 1.62 |
| 70 mM $ZnCl_2$ | 0 | 1.17 ± 1.01 |

The above example demonstrates the surprising efficacy of the lipase-inhibiting agent $ZnCl_2$, at various concentrations, to reduce the irritation caused by prolonged contact of skin with urine and feces under occluded conditions. The above example also demonstrates the role of lipase in contributing to such irritation, and the ability of a lipase-inhibiting agent to thwart this irritant when applied at a level equal to, or above, its minimum inhibitory concentration.

EXAMPLE III

| PATCH | RELATIVE LIPASE ACTIVITY | IRRITATION INDEX |
|---|---|---|
| Control | 100,000 | 4.95 ± 0.45 |
| 100 mM $ZnCl_2$ | — | 0.55 ± 1.23 |
| 100 mM $CaCl_2$ | — | 3.55 ± 1.10 |
| 100 mM $LaCl_3$ | — | 0 ± 0 |

The above example demonstrates the surprising efficacy of various lipase-inhibiting agents to reduce and prevent the irritation of skin caused by prolonged contact with urine and feces under occluded conditions when applied in accordance with the methods of the present invention, when compared to a non-inhibitory salt. The lipase activity is measured only for the control.

EXAMPLE IV

| PATCH | RELATIVE LIPASE ACTIVITY | IRRITATION INDEX |
|---|---|---|
| Control | 127,500 | 6.15 ± 1.08 |
| 10 mM $ZnCl_2$ | 72,500 | 5.55 ± 0.95 |
| 25 mM $ZnCl_2$ | 0 | 0.50 ± 0.82 |
| 50 mM $ZnCl_2$ | 0 | 0.45 ± 0.64 |
| 100 mM $ZnCl_2$ | 0 | 1.75 ± 1.65 |
| 10 mM $FeCl_3.6H_2O$ | 177,500 | 5.55 ± 1.12 |
| 25 mM $FeCl_3.6H_2O$ | 128,750 | 6.15 ± 1.29 |
| 50 mM $FeCl_3.6H_2O$ | 111,350 | 2.60 ± 1.74 |
| 100 mM $FeCl_3.6H_2O$ | 6250 | 0.05 ± 0.16 |

The above example demonstrates the efficacy of the lipase-inhibiting agents in the methods of the present invention, their relative potency, and their effect on lipase activity.

EXAMPLE V

| PATCH | RELATIVE LIPASE ACTIVITY | IRRITATION INDEX |
|---|---|---|
| Control | — | 4.45 ± 0.17 |
| 100 mM $ZnCl_2$ | — | 1.85 ± 0.61 |
| 100 mM $FeCl_3.6H_2O$ | — | 0 |
| 100 mM $SnCl_2$ | — | 0.50 ± 0.16 |

The above example demonstrates the efficacy of various lipase-inhibiting agents to reduce and prevent the irritation of skin caused by prolonged contact with urine and feces under occluded conditions in the methods of the present invention. The lipase activity is not measured.

EXAMPLE VI

In this Example, a non-stool, no-urine pure lipase composition is patched in the hairless mouse model, and then in combination with a lipase-inhibiting agent at the indicated concentrations.

| PATCH | LIPASE ACTIVITY | % REDUCTION LIPASE ACTIVITY |
|---|---|---|
| Lipase Control | 40,320 | N/A |
| 100 mM $CuSO_4$ | 16,500 | 59 |
| 50 mM $CuSO_4$ | 18,500 | 54 |
| 100 mM $SnCl_2$ | 1,250 | 97 |
| 50 mM $SnCl_2$ | 3,000 | 93 |
| 100 mM $CoCl_2$ | 7,750 | 81 |
| 50 mM $CoCl_2$ | 23,750 | 41 |
| 100 mM $FeCl_3.6H_2O$ | 0 | 100 |
| 50 mM $FeCl_3.6H_2O$ | 500 | 99 |
| 100 mM $ZnCl_2$ | 750 | 98 |
| 50 mM $ZnCl_2$ | 1,500 | 96 |

EXAMPLE VII

In this Example, a non-stool, no-urine pure lipase composition is patched in the hairless mouse model, and then in combination with a lipase-inhibiting agent at the indicated concentrations.

| PATCH | LIPASE ACTIVITY | % REDUCTION IN IRRITATION INDEX |
|---|---|---|
| Control | 36,750 | N/A |
| 100 mM $ZnCl_2$ | 1,250 | 97 |
| 100 mM ZnO* | 33,000 | 10 |
| 100 mM $ZnCO_3$* | 35,000 | 5 |
| 100 mM Zn undecylenate* | 10,080 | 73 |

*These were patched as suspensions. $ZnCO_3$ is only capable of forming a 0.08 mM solution; ZnO is only capable of forming a 0.02 mM solution.

Examples VI and VII above, demonstrate the direct role of lipase in causing skin irritation. The above examples also demonstrate the surprising ability of lipase-inhibiting agents to reduce lipase-related irritation in accordance with the methods of the present invention. Example VII also clearly demonstrates that insoluble inorganic metallic salts, which are not capable of providing the free cation, (the ionic portion responsible for lipase inactivation), do not reduce lipase-related irritation to any statistically significant level, and, accordingly, are not useful as lipase-inhibiting agents in the compositions or methods of the present invention.

EXAMPLE VIII

A disposable diaper is prepared according to the teachings of U.S. Pat. Re. 26,151. The diaper consists of a thin backsheet of polyethylene attached to a pad of absorbent airfelt (a matting of cellulose fibers). Combined backsheet and absorbent wadding is overlaid with a compliant, porous, hydrophobic, non-woven fabric web diaper lining (topsheet) having a weight of approximately 17 g per square yard, which comprises 2.0 denier rayon, and which contains 28% by weight of a thermoplastic binder. The combined laminated structure is approximately 15 × 18 inches and is folded into a box pleat configuration by means of a multiplicity of longitudinal folds.

A saturated aqueous solution of ZnCl₂ is prepared at 25° C. The absorbent pad, prior to its assemblage in the above diaper, is completely wetted and allowed to soak in the ZnCl₂ solution. The absorbent pad is allowed to dry and is then used in the assembly of the above diaper.

This diaper is worn as any other, and significantly reduces the frequency of diaper dermatitis.

EXAMPLE IX

The following non-limiting Examples demonstrate the compositions and methods of the present invention.

A hydrophilic vehicle is prepared by mixing 60.0 g of a polyethylene glycol polymer having an average molecular weight of about 400, and about 40.0 g of a polyethylene glycol polymer having a molecular weight of about 3,350. To this mixture is added about 3.75 g of ZnCl₂, and the salt is uniformly dispersed.

This composition is topically applied to the buttocks of a 7.5 kg child suffering from diaper dermatitis. The composition is applied at a rate of about 1.5 mg per square centimeter of skin, and is applied with a frequency of about 4 times to about 6 times per day, preferably with each diaper change. Improvement is noted after about 48 hours, and there is no observable dermatitis at the end of a 7 day period.

Substantially similar results are obtained by replacing the ZnCl₂ in the above hydrophilic vehicle with an equivalent amount of a lipase-inhibiting agent selected from the group consisting of zinc sulfate (the heptahydrate), zinc acetate, zinc nitrate, copper sulfate (the pentahydrate), iron(II)chloride, iron(III)chloride, iron(II)acetate, iron(II)chloride, iron(III)iodate, iron(II)iodide, (tetrahydrate), iron(III)lactate, iron(III)malate, iron(III)nitrate, iron(III)nitrate, iron(II)sulfate (the hydrate), iron(III)sulfate, tin(II)chloride, cobalt chloride, the zinc salts of the monocarboxylic fatty acids having about 6 to about 12 carbon atoms, and mixtures thereof.

Examples X and XI demonstrate the compositions and methods of the present invention. The control and described compositions are patched in accordance with the Hairless Mouse Model, described above.

EXAMPLE X

| PATCH | IRRITATION INDEX | % RED |
|---|---|---|
| Control | 6.75 ± 1.27 | — |
| Same, pretreated with: | | |
| PEG-400 (30 μl) | 5.35 ± 1.33 | 21 |
| 1% ZnCl₂ in PEG-400 | 1.85 ± 1.43 | 73 |
| 2% ZnCl₂ in PEG-400 | 0.25 ± 0.54 | 96 |
| 1% ZnSO₄ in PEG-400* | 4.20 ± 1.14 | 38 |
| 2% ZnSO₄ in PEG-400* | 3.90 ± 1.24 | 42 |
| 90:10 PEG-400:4000 | 2.95 ± 1.01 | 56 |
| 1% ZnCl₂ in 90:10 PEG 400:4000 | 1.00 ± 1.51 | 85 |
| 2% ZnCl₂ in 90:10 PEG 400:4000 | 0.75 ± 1.46 | 89 |
| 1% ZnSO₄ in 90:10 PEG 400:4000* | 1.25 ± 1.23 | 81 |
| 2% ZnSO₄ in 90:10 PEG 400:4000* | 0.80 ± 0.86 | 88 |

*Not completely soluble in this vehicle

EXAMPLE XI

| PATCH | IRRITATION INDEX | % RED |
|---|---|---|
| Control | 1.50 ± 0.99 | — |
| Same, pretreated with: | | |
| 2% ZnCl₂ in PEG-400 | 0.12 ± 0.35 | 92 |
| 2% ZnCl₂ in 90:10 PEG-400:4000 | 0.02 ± 0.07 | 99 |
| 2% ZnCl₂ in 75:25 PEG-400:4000 | 0.10 ± 0.17 | 93 |
| 2% ZnCl₂ in 60:40 PEG-400:4000 | 0.10 ± 0.21 | 93 |
| 2% ZnCl₂ in 50:50 PEG-400:4000 | 0.25 ± 0.63 | 83 |
| 2% ZnCl₂ in 25:75 PEG-400:4000 | 0 | 100 |

As can be seen from the above, the compositions of the present invention, when applied prior to an insult (contact with the urine/feces mixture) provide significant prophylaxis and prevention of the irritation associated with such insult.

What is claimed is:

1. A method of treating and preventing diaper rash, or diaper dermatitis, caused by prolonged contact of human skin with body waste, which method comprises topically applying to an area in need of such treatment or prevention a minimum inhibitory concentration of a pharmaceutically-acceptable lipase-inhibiting agent selected from the group consisting of water-soluble salts of cadmium, cobalt, lead, mercury, molybdenum, nickel, silver, lanthanum, tin, zinc and iron.

2. A method according to claim 1 wherein the lipase-inhibiting agent is selected from the group consisting of the water-soluble salts of cobalt, lanthanum, tin, zinc, iron, and mixtures thereof.

3. A method according to claim 2 wherein the lipase-inhibiting agent is selected from the group consisting of zinc chloride, zinc acetate, zinc nitrate trihydrate, zinc nitrate hexahydrate, zinc sulfate, zinc sulfate heptahydrate, zinc sulfate hexahydrate, iron(II)chloride, iron(II)chloride tetrahydrate, iron(III)chloride, iron(III)chloride monohydrate, iron(III)chloride hexahydrate, iron(II)lactate, iron(III)lactate, iron(III)malate, iron(II)nitrate, iron(III)nitrate hexahydrate, iron(III)nitrate.9H₂O, iron(II)sulfate and its hydrates, iron(III)sulfate and its hydrates, tin chloride, cobalt chloride and lanthanum chloride.

4. A method according to claim 2 wherein the lipase-inhibiting agent is selected from the zinc salts of the monocarboxylic fatty acids having from about 6 to about 12 carbon atoms.

5. A method according to claim 4 wherein the zinc salt of the monocarboxylic fatty acid has from about 8 to about 10 carbon atoms.

6. A method according to claim 3 wherein the lipase-inhibiting agent is selected from the group consisting of zinc chloride, zinc sulfate, iron(II)chloride, iron(III)chloride, tin chloride, and mixtures thereof.

7. A method according to claim 6 wherein the lipase-inhibiting agent is zinc chloride.

8. A method according to claim 2 wherein the lipase-inhibiting agent is applied at a concentration of about 10 mM or greater.

9. A method according to claim 3 wherein the lipase-inhibiting agent is applied at a concentration of about 10 mM or greater.

10. A method according to claim 6 wherein the lipase-inhibiting agent is applied at a concentration of about 10 mM or greater.

11. A method according to claim 7 wherein the lipase-inhibiting agent is applied at a concentration of about 10 mM or greater.

12. A method according to claim 2 wherein the lipase-inhibiting agent is applied at a concentration of about 50 mM or greater.

13. A method according to claim 3 wherein the lipase-inhibiting agent is applied at a concentration of about 50 mM or greater.

14. A method according to claim 6 wherein the lipase-inhibiting agent is applied at a concentration of about 50 mM or greater.

15. A method according to claim 11 wherein the lipase-inhibiting agent is applied at a concentration of about 50 mM or greater.

16. A method according to claim 2 wherein the lipase-inhibiting agent is applied at a concentration of about 100 mM or greater.

17. A method according to claim 3 wherein the lipase-inhibiting agent is applied at a concentration of about 100 mM or greater.

18. A method according to claim 6 wherein the lipase-inhibiting agent is applied at a concentration of about 100 mM or greater.

19. A method according to claim 11 wherein the lipase-inhibiting agent is applied at a concentration of about 100 mM or greater.

20. In a disposable diaper comprising:
   (1) an absorbent core,
   (2) a topsheet, said topsheet superposed or co-extensive with one face of said core, and
   (3) a liquid impervious backsheet, said backsheet superposed or co-extensive with the face of said core opposite the face covered by said topsheet;
the improvement comprising incorporating therein a lipase-inhibiting agent at its minimum inhibitory concentration or greater, said lipase-inhibiting agent being selected from the group consisting of water-soluble salts of cadmium, cobalt, lead, mercury, molybdenum, nickel, silver, lanthanum, tin, zinc and iron.

21. An article according to claim 20 wherein the lipase-inhibiting agent is incorporated into the absorbent core.

22. An article according to claim 20 wherein the lipase-inhibiting agent is incorporated into the topsheet.

23. In a disposable wipe especially adapted for removing fecal matter from skin comprising:
   an absorbent fibrous material; the improvement comprising releasably incorporating into said absorbent material an amount of lipase-inhibiting agent sufficient to deliver a minimum inhibitory concentration of said agent to human skin when used to remove fecal matter, said lipase-inhibiting agent being selected from the group consisting of water-soluble salts of cadmium, cobalt, lead, mercury, molybdenum, nickel, silver, lanthanum, tin, zinc and iron.

24. In a disposable wipe especially adapted for removing fecal matter from skin comprising:
   (1) an absorbent fibrous material; and
   (2) a feces-impermeable backing, said backing superposed or at least partially co-extensive with one face of said absorbent material;
the improvement comprising releasably incorporating into said absorbent material an amount of lipase-inhibiting agent sufficient to deliver a minimum inhibitory concentration of said agent to human skin when used to remove fecal matter, said lipase-inhibiting agent being selected from the group consisting of water-soluble salts of cadmium, cobalt, lead, mercury, molybdenum, nickel, silver, lanthanum, tin, zinc and iron.

25. An article according to claim 24 wherein the absorbent material has additionally releasably incorporated therein a safe and effective amount of skin cleansing agent.

26. An article according to claim 25 wherein the cleansing agent is an oleaginous cleansing agent.

27. A method of treating and preventing diaper rash, or diaper dermatitis, caused by prolonged contact of human skin with body waste comprising contacting the area in need of such treatment with an article according to claim 23.

* * * * *